United States Patent [19]

Kress et al.

[11] Patent Number: 5,397,799
[45] Date of Patent: Mar. 14, 1995

[54] CRYSTALLINE SALT OF 4-(DI-N-PROPYL)AMINO-6-AMINOCARBONYL-1,3,4,5-TETRAHYDROBENZ[CD]-INDOLE

[75] Inventors: Thomas J. Kress; David L. Varie, both of Indianapolis, Ind.

[73] Assignee: Eli Lilly and Company, Indianapolis, Ind.

[21] Appl. No.: 64,539

[22] Filed: May 19, 1993

Related U.S. Application Data

[62] Division of Ser. No. 485,185, Feb. 26, 1990, abandoned.

[51] Int. Cl.⁶ .................. A61K 31/40; C07D 209/62
[52] U.S. Cl. ............................ 514/411; 548/436
[58] Field of Search .................. 548/436; 514/411

[56] References Cited

U.S. PATENT DOCUMENTS

| | | | |
|---|---|---|---|
| 4,110,339 | 8/1978 | Bach et al. | 548/436 |
| 4,576,959 | 3/1986 | Flaugh | 514/411 |
| 4,745,126 | 5/1988 | Leander | 514/411 |

OTHER PUBLICATIONS

Leanna, et al., *Tet. Lett.*, 30, p. 3935 (1989).
Sugi and Mitsui, *Bull. Chem. Soc. Jap.*, 43, p. 1489 (1970).
Schoenberg and Heck, *Journal of Organic Chemistry*, 39, p. 3325 (1974).
Schoenberg, Bartoletti and Heck, *Journal of Organic Chemistry*, 39, p. 3318 (1974).
Physicians' Desk Reference, Medical Economics Co 1989, pp. 1214 & 1415.

*Primary Examiner*—Mary C. Lee
*Assistant Examiner*—Jacqueline Haley
*Attorney, Agent, or Firm*—Steven P. Caltrider; David E. Boone

[57] ABSTRACT

Crystalline 4-(di-n-propyl)amino-6-aminocarbonyl-1,3,4,5-tetrahydrobenz[cd]indole hippurate and its method of preparation and use are provided.

10 Claims, No Drawings

CRYSTALLINE SALT OF 4-(DI-N-PROPYL)AMINO-6-AMINOCARBONYL-1,3,4,5-TETRAHYDROBENZ[CD]-INDOLE

This application is a division of application Ser. No. 07/485,185, filed Feb. 26, 1990, abandoned.

FIELD OF THE INVENTION

This invention relates to the field of pharmaceutical chemistry and involves a crystalline salt of a substituted tetrahydrobenz[cd]indole and its use.

BACKGROUND OF THE INVENTION

Flaugh in U.S. Pat. No. 4,576,959 discloses that 6-substituted-4-dialkylaminotetrahydrobenz[c,d]indoles and their pharmaceutically acceptable salts are central serotonin agonists, useful for treating depression, obesity, alcoholism, smoking, or senile dementia. Leander in U.S. Pat. No. 4,745,126 further discloses that certain 4-dialkylamino-6-aminocarbonyl-1,3,4,5-tetrahydrobenz[c,d]indoles and their pharmaceutically acceptable acid addition salts are useful in treating anxiety.

It is recognized in the art that it is particularly advantageous that a solid pharmaceutical substance be crystalline, rather than amorphous. Typically, crystalline solids more easily purified, more easily characterized, and more pharmaceutically elegant than solids which are amorphous. This invention provides a crystalline acid addition salt of a particularly preferred compound of Flaugh and of Leander.

SUMMARY OF THE INVENTION

This invention provides 4-(di-n-propyl)amino-6-aminocarbonyl-1,3,4,5-tetrahydrobenz[cd]indole hippurate. In another embodiment, this invention involves a pharmaceutical formulation comprising said compound together with a pharmaceutical excipient, diluent, or carrier therefor. A further embodiment of this invention concerns a method for treating conditions in a mammal requiring enhancement of serotonin function in the body by administering an amount of said compound sufficient to enhance serotonin function. Another embodiment of the present invention concerns a method of treating depression in humans comprising administering to a depressed individual an antidepressant dose of said compound. A further embodiment of this invention concerns a method of treating anxiety in humans comprising administering to a human susceptible to or suffering from anxiety an antianxiety dose of said compound. In another embodiment the present invention involves a method for preparing the crystalline hippurate by dissolving the indole and hippuric acid in isopropyl alcohol and then crystallizing the hippurate.

DETAILED DESCRIPTION OF THE INVENTION

All temperatures discussed herein are expressed in degrees Celsius. The base compound is (±)4-(di-n-propyl)amino-6-aminocarbonyl-1,3,4,5-tetrahydrobenz[c,d]indole, which has the structure:

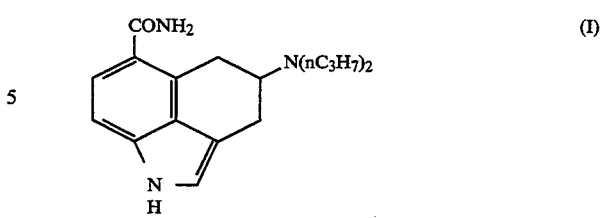

The acid addition salt of this invention is formed by contacting the base compound of Formula I with hippuric acid, also known as N-benzoylglycine and also known as benzamidoacetic acid, which has the structure:

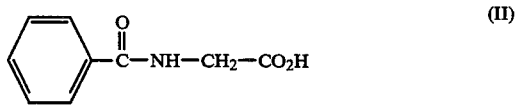

The acid addition salt is, therefore, 4-(di-n-propyl)amino-6-aminocarbonyl-1,3,4,5-tetrahydrobenz[cd]indole hippurate. The salt corresponds to a one to one molar ratio of the indole to hippuric acid.

The hippurate salt of the compound of Formula I has the particularly advantageous property of crystallinity, unlike numerous other acid addition salts of Formula I that have been prepared. As a crystalline substance, the hippurate salt can be readily prepared in high purity by dissolving the base compound (indole) in an inert solvent or mixture of inert solvents, adding hippuric acid, and allowing the thus formed salt to crystallize. The solvent of choice should be capable of dissolving the hippuric acid and indole but should not chemically react with either. The solvent should have a low solubility for the hippurate salt. Preferably the solvent also has a low toxicity level. Solvents include isopropyl alcohol, acetone, ethanol, isopropyl alcohol and water mixture, methyl ethyl ketone, butanol, tetrahydrofuran, dimethyl formamide, acetonitrile, and a mixture of isopropyl alcohol and ethylacetate. Preferred solvents include isopropyl alcohol, a mixture of isopropyl alcohol and water, and ethanol. If desired, the product can be further purified by recrystallizing it one or more times from such a solvent. Alternatively a first solvent such as isopropyl alcohol can be used in a first crystallization followed by the use of a second solvent such as ethanol in at least one subsequent crystallization step. If desired, the mother liquor from such subsequent crystallization steps can be recycled and used as the solvent to dissolve the hippurate.

It has been found that the hippurate can retain solvent apparently in the crystal lattice. It has also been found that water appears to be preferentially retained compared to certain other solvents. Therefore to minimize any retention of other solvents by the salt, it is preferred that water be added to the solvent when compatible. For example, it is preferred that at least about 5 percent, more preferably 10 percent, and most preferably at least about 15 percent by volume water be used when isopropyl alcohol is used as the primary solvent. As is typical, it may be necessary to heat the solvent in order to maximize dissolution of the salt. By crystallization the salt can be thus prepared in purity exceeding 99%. Other salt forms which are not crystalline are not so readily purified and frequently require the employment of expensive, tedious chromatographic techniques for their purification.

Organic and pharmaceutical chemists will recognize that the hippurate of the compound of Formula I contains one chiral center. The compound of this invention is useful whether it exists substantially as the R enantiomer, substantially as the S enantiomer, or as a mixture of the two enantiomers. The preferred embodiment is the hippurate of the compound of Formula I which is a substantially pure enantiomer, especially the R enantiomer.

If it is desired to prepare the racemic mixture of 4-(di-n-propyl)amino-6-aminocarbonyl-1,3,4,5-tetrahydrobenz[cd]indole hippurate, then the base compound can be prepared by the method disclosed by Flaugh, supra. However, the following method can be used to prepare a single enantiomer of the base compound, which may then be used to prepare a single enantiomer of the hippurate salt.

The following pair of enantiomers of 1-benzoyl-4,5-epoxy-1,2,2a,3,4,5-hexahydrobenz[cd]indole can be selectively prepared by the methods of Leanna, et al., *Tet. Lett.*, 30, no. 30, pp. 3935–3938 (1989).

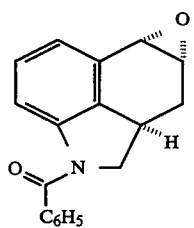

(III)a

(III)b

The reaction of the racemic mixture of III$_a$ and III$_b$ with a primary amine containing a chiral center such as S-1-phenylethylamine produces a pair of diastereomers of the formulae:

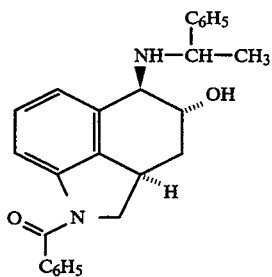

IVa

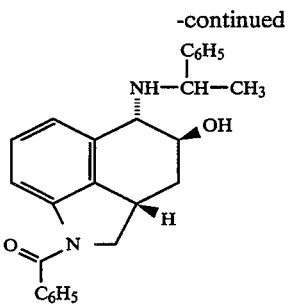

IVb

The diastereomers can be separated by a number of methods frequently used in the art such as chromatography and selective crystallization.

A particularly advantageous method of preparing a substantially pure diastereomer of Formula IV$_a$ in a single step is as follows. The reaction is conducted in n-butanol at a concentration of about 1 gram of the epoxide per 9 milliliters of solvent at about 90° C. for about 16 hours. Upon being cooled to about room temperature, the diastereomer of Formula IV$_b$ remains in solution, while the diastereomer of Formula IV$_a$ crystallizes and can be collected by filtration.

For simplicity of discussion, the subsequent intermediates and products shown below are those that result from the compound of Formula IV$_a$. Of course, the use of R-1-phenylethylamine instead of S-1-phenylethylamine in the above reaction will result in the selective crystallization of the compound which is the mirror image of Formula IV$_a$, and the use thereof in this synthesis results in subsequent intermediates and products which are the enantiomers of those shown below. Also other optically active primary amines in addition to 1-phenylethyl amine could be used.

The next step in the preparation of the preferred starting material for the compounds of the invention is to form an aziridine of Formula V.

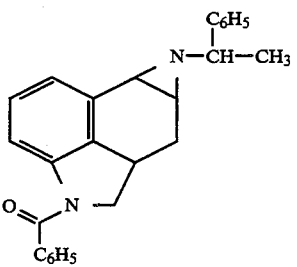

V

Several methods of forming aziridines from beta amino alcohols are known to the art. A preferred method is the reaction of the compound of Formula IV$_a$ with triethylamine and methanesulfonyl chloride in dichloromethane. The following compound can be isolated from the reaction solution:

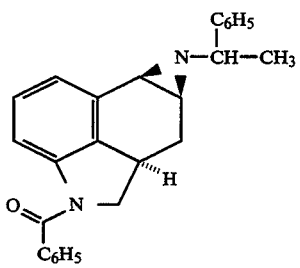

Va

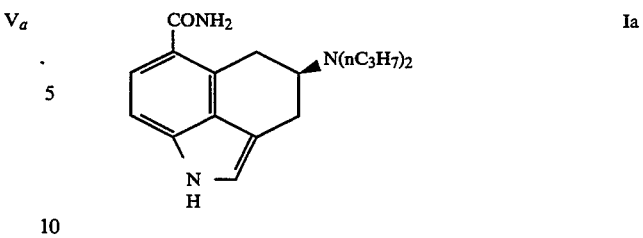

Ia

The azridine of Formula V is hydrogenolyzed over a noble metal catalyst such as palladium. It is important that the opening of the aziridine to form the secondary amine be substantially regiospecific, i.e. the aziridine should be opened to form substantially the 4-amino compound rather than the 5-amino compound. One such method is catalytic hydrogenolysis as taught by Y. Sugi and S. Mitsui, *Bull. Chem. Soc. Jap.*, 43, pp. 1489–1496 (1970). The preferred solvent is a mixture of acetic acid and methanol, and the reaction is conducted under approximately one atmosphere of hydrogen gas using a noble metal catalyst, preferably palladium. The reaction mixture is stirred at −5° C. until the aziridine is consumed, as determined by thin layer chromatography or liquid chromatography. The product of this hydrogenolysis is a secondary amine, 1-benzoyl-4-(S-1-phenylethyl)amino-1,2,2a,3,4,5-hexahydrobenz[cd]indole, which need not be isolated. The hydrolysis is continued at about 55° C. under about 1 atmosphere of hydrogen gas until the secondary amine is consumed, as determined by thin layer chromatography or liquid chromatography. Isolation, for example by crystallization, affords the substantially enantiomerically pure compound of Formula VI which is:

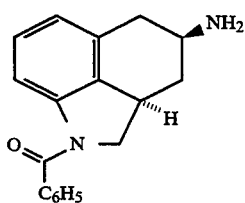

VI

The compound of Formula VII can be prepared from the compound of Formula VI by alkylation with propyl iodide in the presence of a base such as potassium carbonate in a solvent such as acetonitrile, followed by iodination by iodine and orthoperiodic acid in the presence of an acid such as sulfuric acid or trifluoroacetic acid in a solvent such as aqueous acetic acid. Alternatively, iodination may precede alkylation.

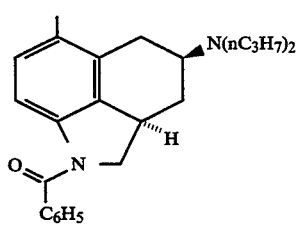

VII

The following enantiomer of the compound of Formula I can be prepared from the compound of Formula VII by reaction with an approximately equimolar mixture of carbon monoxide and ammonia in the presence of a catalyst, preferably a palladium catalyst such as bis(triphenylphosphine)palladium chloride or bis(triphenylphosphine)palladium bromide. The catalyst is preferably present in a ratio of about 0.05 mole per mole of reaction substrate. The preferred solvent is toluene, and the concentration of the reactant is about 0.5 to about 2.0 grams per 100 milliliters of solvent. The reaction vessel is sealed and the reaction mixture stirred at approximately 100° C. for approximately 6 hours. The use of such catalysts for the reaction of arylhalides with carbon monoxide is disclosed by Schoenberg and Heck, *Journal of Organic Chemistry*, 39, p. 3325 (1974) and Schoenberg, Bartoletti and Heck, *Journal of Organic Chemistry*, 39, p. 3318, (1974). The benzoyl group can then be removed by any of a number of methods known to the art, but preferably by reaction with approximately 4 equivalents of n-butyl lithium in freshly distilled tetrahydrofuran. The deprotection reaction is conducted at about −78°. The reaction is quenched by the addition of 1:1 (volume:volume) water and tetrahydrofuran, and the resulting 4-(di-n-propyl)amino-6-aminocarbonyl-1,2,2a,3,4,5-hexahydrobenz[cd]indole is isolated by evaporation of the tetrahydrofuran, extraction from the aqueous phase into a solvent such as methylene chloride, and evaporation of the solvent. Oxidation of the hexahydrobenz-[cd]indole by reaction with manganese dioxide in acetic acid by the method disclosed by Flaugh in U.S. Pat. No. 4,576,959 or palladium on carbon in methanol affords the desired 4-(di-n-propyl)amino-6-aminocarbonyl-1,3,4,5-tetrahydrobenz[cd]indole.

The preparation of 4-(di-n-propyl)amino-6-aminocarbonyl-1,3,4,5-tetrahydrobenz[c,d]indole hippurate is accomplished by dissolving the base compound of Formula I in an inert solvent as discussed hereinabove and contacting it with about one or more equivalents of hippuric acid. The contacting can be conducted at a temperature of about 0° C. to about 100° C., preferably from about 0° C. to about 25° C. Suitable solvents include those discussed hereinabove.

The following examples are provided to illustrate the present invention and are not to be construed as limiting the scope thereof.

EXAMPLE 1

Hippuric acid (0.60 grams, 3.3 millimoles) was combined with acetone (30 milliliters) and heated to 45° C. to dissolve the hippuric acid. (R)-4-(di-N-propyl)amino-6-aminocarbonyl-1,3,4,5-tetrahydrobenz[cd]indole (1.0 g. 3.3 mmol) dissolved in acetone (10 ml) was added dropwise to the 45° C. solution of hippuric acid. The mixture was cooled with stirring under nitrogen. After 30 minutes at 25° C., less than 1 milligram of seed crystals were added. Within one minute the solution was cloudy and crystals began to form and fall to the bottom of the flask. The mixture was stirred 30 minutes and then allowed to stand one hour. The mixture was filtered and the solid washed with reagent grade acetone. The solid was dried by air flow and then dried under vacuum to give 1.32 grams of white solid. Analysis of the solid gave the following results.

Melting point: 192°–194° C.
UV (ethanol): 240 nm ($\epsilon$=42,000), 281 nm ($\epsilon$=5650)
IR (KBr): 3141, 3135, 1653, 1603, 1578, 1544, 1384, 1367, 1357, 1279, 1254
$[\alpha]_D = -38.7°$ (methanol)
MS: m/e =300, 180

| Analysis: ($C_{27}H_{34}O_4N_4$) | C | H | N |
|---|---|---|---|
| Theory | 67.76 | 7.16 | 11.71 |
| Found | 67.59 | 6.93 | 11.43 |

X-Ray Crystallography provided unit cell dimensions in Å of: a=10.2974(5); b=12.0619(3); 20.1382(6). with $\alpha$=90°, $\beta$=90°, $\delta$=90° volume=2501.29±1.45 $Å^3$

EXAMPLE 2

2.70 grams (15 mmoles) of hippuric acid were added to 40 ml of isopropyl alcohol. The mixture was heated to 70° C. to dissolve the hippuric acid. To the hot solution were added approximately 4.5 g (14.9 m moles) of (S)-4-(di-n-propyl)amino-6-aminocarbonyl-1,3,4,5-tetrahydrobenz[cd]indole dissolved in 25 ml of isopropyl alcohol. The solution was allowed to cool to room temperature, after 30 minutes white crystals formed. The mixture was stirred for 2 hours and then allowed to stand overnight. The mixture was filtered and the cake washed with isopropyl alcohol. The cake was dried at 40° C. for 5 hours to yield 5.5 g of solid. By NMR the solid contained about 3 weight percent isopropyl alcohol. The filtrate was concentrated to a foam, extracted with an aqueous base/methylene chloride mixture, and dried 24 hours at 50° C. under vaccum. 5.4 g of the solid were dissolved in 65 ml of a mixture of isopropyl alcohol and water (90:10, v:v) at 85° C. The solution was allowed to cool to 25° C. with stirring. The flask was scratched and seed crystals of the solid material which had been dissolved were added. The solution was placed in a refrigerator at 5° C.; after one hour crystals had formed. Scratching the flask caused more crystal formation. The mixture was stored at 5° C. overnight and filtered. The solid was washed with isopropyl alcohol and vacuum dried at 50° C. for 24 hours to provide 3.78 g of white solid. Analysis of the white solid provided the following data:

Melting point: 190.5°–192° C.
IR (KBr): 3458, 3134, 2975, 1655, 1604, 1545, 1384, 1278 $cm^{-1}$.
$[\alpha]_D = +39.4°$ (c=0.1, methanol)
UV (ethanol): 278 nm ($\epsilon$=4880), 240 nm ($\epsilon$=44000)
Analysis ($C_{27}H_{34}N_4O_4$)

| Analysis ($C_{27}H_{34}N_4O_4$) | C | H | N |
|---|---|---|---|
| Theory | 67.76 | 7.16 | 11.71 |
| Found | 68.24 | 7.46 | 11.40 |

EXAMPLE 3

A racemic mixture of (RS)-4-(di-n-propyl)amino-6-aminocarbonyl-1,3,4,5-tetrahydrobenz[cd]indole hippurate was prepared by combining equal amounts of the substantially pure enantiomeric indole hippurates. 150 mg of (R)-4-(di-n-propyl)amino-6-aminocarbonyl-1,3,4,5-tetrahydrobenz[cd]indole hippurate were combined with 150 mg of the corresponding (S)-indole hippurate. The mixture was slurried in 10 ml of 0.2 normal HCl. 10 ml of ethyl acetate were added followed by 10 ml of 5 normal sodium hydroxide. The aqueous and organic layers were separated and the aqueous layer was extracted with 10 ml of ethyl acetate. The combined ethyl acetate layers were washed with 10 ml of 2 normal sodium hydroxide. The liquid was dried with sodium sulfate and the ethyl acetate removed by vacuum to obtain 168 mg of white solid which is the racemic free base. 3 ml of isopropyl alcohol were added to the solid product and crystals formed. The cyrstals were dissolved by heating on a steam bath. This solution was added to a solution containing 100 mg (one equivalent) of hippuric acid in 1 ml isopropyl alcohol at 70° C. The solution was allowed to cool with stirring. A precipitate formed after 30 minutes. After 4 hours of stirring the mixture was filtered and the solid washed with isopropyl alcohol. Vacuum drying gave 239 mg of white solid which had the following properties.

Melting Point: 175°–177° C.
$[\alpha]_D = 0.06°$ (methanol)

The composition of the present invention is useful in the enhancement of serotonin function in mammals. The indole component of the composition has been found to have selective affinity to block 5HT1A receptors.

The composition of this invention may be administered, perferably orally, about once per day to about 4 times per day, in an effective dose to an individual suffering from or susceptible to anxiety. An effective dose is normally between about 1 and about 50 milligrams per kilogram of body weight.

The present composition can also be used to treat depression and consumptive disorders such as obesity, alcoholism and smoking and senile dementia. The effective dosage, normally administered orally, generally ranges from about 0.1 mg to about 50 mg per kilogram of body weight depending on the affliction.

We claim:
1. A compound which is (R)-4-(di-n-propyl)amino-6-aminocarbonyl-1,3,4,5-tetrahydrobenz[c,d]indole hippurate.
2. A compound which is (S)-4-(di-n-propyl)amino-6-aminocarbonyl-1,3,4,5-tetrahydrobenz[c,d]indole hippurate.
3. A pharmaceutical formulation comprising the compound of claim 1 together with a pharmaceutically acceptable excipient, diluent, or carrier therefor.
4. A pharmaceutical formulation comprising the compound of claim 2 together with a pharmaceutically acceptable excipient, diluent, or carrier therefor.
5. A method of treating anxiety in humans comprising administering to a human susceptible to or suffering from anxiety an antianxiety dose of the compound of claim 1.
6. A method of treating anxiety in humans comprising administering to a human susceptible to or suffering from anxiety an antianxiety dose of the compound of claim 2.
7. A method for treating a condition in a mammal which requires enhancement of serotonin function by administering to said mammal an amount of the compound of claim 1 sufficient to enhance serotonin function.

8. A method for treating a condition in a mammal which requires enhancement of serotonin function by administering to said mammal an amount of the compound of claim 1 sufficient to enhance serotonin function.

9. A method of treating depression in humans comprising administering to a depressed individual an antidepressant dose of the compound of claim 1.

10. A method of treating depression in humans comprising administering to a depressed individual an antidepressant dose of the compound of claim 2.

* * * * *